United States Patent
Törmälä et al.

(10) Patent No.: US 7,419,681 B2
(45) Date of Patent: Sep. 2, 2008

(54) METHOD TO ENHANCE DRUG RELEASE FROM A DRUG-RELEASING MATERIAL

(75) Inventors: Pertti Törmälä, Tampere (FI); Esa Suokas, Tampere (FI); Minna Veiranto, Pirkkala (FI); Nureddin Ashammakhi, Vantaa (FI)

(73) Assignee: Bioretec, Ltd., Tampere (FI)

( * ) Notice: Subject to any disclaimer, the term of this patent is extended or adjusted under 35 U.S.C. 154(b) by 676 days.

(21) Appl. No.: 11/000,987

(22) Filed: Dec. 2, 2004

(65) Prior Publication Data

US 2006/0121082 A1 Jun. 8, 2006

(51) Int. Cl.
*A61F 2/00* (2006.01)
*A61F 2/06* (2006.01)

(52) U.S. Cl. .......................... 424/423; 623/1.1

(58) Field of Classification Search ................ 424/422, 424/423; 606/194; 623/1.1, 1.42, 1.45, 16.11, 623/20.17
See application file for complete search history.

(56) References Cited

U.S. PATENT DOCUMENTS

| | | | |
|---|---|---|---|
| 4,743,257 A | | 5/1988 | Tormala et al. |
| 5,556,595 A | * | 9/1996 | Suzuki et al. ................ 422/32 |
| 5,834,582 A | * | 11/1998 | Sinclair et al. ............... 528/354 |
| 5,977,204 A | * | 11/1999 | Boyan et al. ................ 523/113 |
| 6,280,478 B1 | * | 8/2001 | Richter et al. ............ 623/23.56 |
| 6,406,498 B1 | | 6/2002 | Tormala et al. |
| 6,579,533 B1 | * | 6/2003 | Tormala et al. ............. 424/426 |
| 7,378,144 B2 | * | 5/2008 | DeMeo et al. .............. 428/212 |
| 2004/0093008 A1 | * | 5/2004 | Zamore ...................... 606/194 |
| 2004/0171323 A1 | * | 9/2004 | Shalaby ..................... 442/123 |
| 2004/0181271 A1 | * | 9/2004 | DeSimone et al. .......... 623/1.1 |

FOREIGN PATENT DOCUMENTS

| EP | 1 157 708 A2 | * | 11/2001 |
|---|---|---|---|
| EP | 1607109 | | 12/2005 |
| WO | WO 2005/007209 | | 1/2005 |

OTHER PUBLICATIONS

"Extrusion—Wikipedia," http://en.wikipedia.org/wiki/Extrusion, pp. 1-3, site accessed Feb. 3, 2008.*
International Search Report, PCT Application No. PCT/EP2005/012919 issued May 4, 2006 (PCT counterpart of U.S. Appl. No. 11/000,987).

* cited by examiner

*Primary Examiner*—Sharon E. Kennedy
(74) *Attorney, Agent, or Firm*—Kenyon & Kenyon LLP

(57) ABSTRACT

A method of enhancing the drug release rate from a composite material. The composite material includes a synthetic, bioabsorbable polymer matrix and a drug particle phase dispersed therein. The release rate of the drug from the polymer matrix is enhanced by orienting the composite material. The drug release rate of the oriented composite material is greater than the drug release rate from an otherwise comparable non-oriented composite material.

15 Claims, 4 Drawing Sheets

METHOD TO ENHANCE DRUG RELEASE FROM A DRUG-RELEASING MATERIAL

FIELD OF THE INVENTION

The present invention relates to a method of enhancing drug release from a composite material by orienting the composite material.

BACKGROUND OF THE INVENTION

Bioabsorbable surgical devices made from bioabsorbable polymers are becoming more frequently used in the medical profession in bone-to-bone, soft tissue-to-bone or soft tissue-to-soft tissue fixation. Numerous publications describe bioabsorbable devices for tissue fixation applications. (See e.g. U.S. Pat. Nos. 4,655,203; 4,743,257; 4,863,472; 5,084,051; 4,968,317; EPO Pat. No. 449,867; U.S. Pat. No. 5,562,704; PCT/FI 96/00351; PCT/FI 96/00511; FI Pat. Appl. No. 965111; U.S. patent application Ser. No. 08/873,174; U.S. patent application Ser. No. 08/887,130; U.S. patent application Ser. No. 08/914,137; and U.S. patent application Ser. No. 08/921,533.

In the case of bioabsorbable tissue fixation devices, surgeons would prefer to use such devices that eventually resorb and disappear from the body after their function during tissue fixation and healing has been served. Such a device made from a bioabsorbable polymer must have sufficient strength and stiffness for effective tissue fixation and must retain sufficient strength to perform its function during the tissue healing process before being absorbed by the body.

It is advantageous to mix different additives, like drugs, into bioabsorbable polymers to modify their properties and/or to achieve useful properties. Antibiotics are typical additives, which can promote clinical performance of the surgical device and can be released from the device in vivo to counter an infection and/or prevent the colonization of bacteria on the surface of the device.

A well-known procedure for treatment of bone infections is the use of polymethymethacrylate (PMMA) beads that contain antibiotics (e.g. SEPTOBAL® beads). Such beads are placed in surgical voids and thereby fill the voids, as well as provide local bactericidal levels of antibiotic. However, even these PMMA beads have disadvantages. First, they usually can only provide bactericidal levels of antibiotic for about a few weeks, so parenteral antibiotic must also be administered. Second, the PMMA beads must eventually be removed surgically, resulting in further trauma to the patient's body. Third, PMMA beads do not facilitate new bone formation in any way. Additionally, PMMA bends act as fillers and they have no effect as a bone fracture fixation device. Antibiotics may also be mixed with a PMMA bone cement, which, however, is a non-absorbable biomaterial.

A long-standing need exists for improved methods of preventing and treating infections in fixation of bone fractures and osteotomies. An especially long-standing need exists for strong, totally synthetic, bioabsorbable drug-releasing implants for preventing and/or treating infections in fixation of bone fractures and osteotomies, which implants give a secure fixation of bone fracture and prevent and/or treat infections by starting rapid continuous antibiotic release in therapeutic concentrations and also by releasing antibiotics over several weeks or months.

The principles of synthetic, bioabsorbable polymeric fracture fixation devices, which can contain and release antibiotics, were described for the first time in the late 1980s. For example, U.S. Pat. No. 4,610,692 describes a method of producing sintered tricalcium phosphate implants for filling bone cavities and for fixing bone fragments in a living body, which comprises: mixing tricalcium phosphate with at least one substance which under heat sufficiently high to bake said tricalcium phosphate forms a gas; shaping the thus-formed mixture into shaped bodies thereof; baking the shaped bodies at a temperature sufficiently high to cause gas formation from said substance, thereby forming pores in said shaped bodies; impregnating said shaped porous bodies with a therapeutically-active ingredient, thereby distributing the same in the pores; and coating at least a part of one of said shaped, porous bodies having said therapeutically-active ingredient distributed therein, with a coating of a predetermined thickness of a biodegradable substance, whereby the time of absorption of said therepeutically-active ingredient is controlled by the thickness of said biodegradable substance. Sintered ceramic bodies, however, are brittle and mechanically weak, which is a risk factor when such materials are used in manufacturing of implants for fixing of bone fragments. Additionally, the biodegradable coating on the porous body may prevent bone growth into the pores of the tricalcium phosphate body as long as the coating is uniform. Therefore, there is not an advantageous synergism of release of antibiotic and growth of bone tissue into contact with absorbing ceramic filler phase. Also, the therapeutically-active ingredient is not mixed with a bioabsorbable matrix in this case, but is distributed among the pores within the tricalcium phosphate body.

PCT/FI 88/00108 and PCT/FI 90/00113 describe absorbable, self-reinforced polymeric materials and absorbable fixation devices for different surgical purposes for fixation of different tissues or parts of tissues by internal or external fixation techniques. These references describe that materials of the invention can contain different additives, like antibiotics, which can give the materials special functional advantages. However, no information is given of antibiotic release from such materials and implants.

U.S. Pat. No. 4,347,234 describes a collagen based drug delivery system which is resorbable in the body. Even if this drug delivery system can be used in the treatment of osteomyelitis, it contains a substantial amount of animal or human-based collagen. Biological tissue-based biomaterials have aroused concern because of the risk of delivering host based diseases, like viral or prion infections, into the human patients (See e.g. S. Yamada et al. Neurosurgery, 34 (4) 1994, p. 740-743). It is well known that collagen based materials became flexible in tissue conditions because of water absorption. Therefore, they cannot be applied as fracture fixation materials. Therefore, a totally synthetic drug-delivery system should be preferable.

Bioabsorbable polymeric drug delivery systems for the treatment of chronic osteomyelitis were described further in 1991-1992 by several groups. C. Teupe et al., in "Ciprofloxacin-impregnated poly-L-lactic acid drug carrier", Arch. Orthop. Trauma Surg. 112 (1992) 33-35 and S. Winckler et al., in "Resorbierbare Antibiotikumträger zur lokalen Behandlung der chronischen Osteitis—Polyglykolsäure/Poly-L-Laktid als Träger, Experimentelle Untersuchungen in vitro", Langenbecks Arch. Chir. 377 (1992) 112-117, described bioabsorbable polyglycolic acid (PGA) and poly-L-lactic (PLLA) cylinders containing antibiotic ciprofloxacin which is released from cylinders in hydrolytic and in vivo conditions during several weeks in therapeutic doses. No information is given of long lasting, therapeutic level release of antibiotics from these implants, which were manufactured from antibiotic impregnated fibers with a slow and complicated sintering process.

U.S. Pat. No. 5,268,178 describes bioabsorbable antibiotic implants comprising at least one antibiotic drug. U.S. Pat. No. 5,281,419 describes an antibiotic impregnated fracture fixation device and antibiotic impregnated drug delivery polymer. However, no indication of therapeutic release level of antibiotics of these implants is given in either reference.

Di Silvio and Bonfield describe a drug delivery system comprising gelatin for the combined release of therapeutic levels of both gentamicin and growth hormone in "Biodegradable drug delivery system for the treatment of bone infection and repair," *Int. Conf. Adv. Biomater. and Tissue Eng.*, June 14-19, Capri, Italy, Book of Abstracts, 1998, p. 89-90. Even if this system combines a sustained release of antibiotics in combination with a bone stimulating factor, this system releases gentamicin only up to 14 days. This is in many cases too short of an influence time of an antibiotic. Effective healing of an osteomyelitis may need antibiotic(s) treatment of at least several weeks (see e.g. L. Dahl et al., *Scand. J. Infect. Dis.*, 30 (6), (1998) p. 573-7 or S. Veng et al., *J. Trauma*, 46 (1) (1999) p. 97-103). Additionally, gelatin based systems are mechanically weak and cannot be used in the form of bone fracture fixation implants. Also, as mentioned above, animal based biomaterials, like gelatin, have aroused concern of the risk of delivering animal based diseases, like viral infections, into human patients. Further, the release of a bone growth promoting factor from the drug delivery system was limited to 2 weeks, which is far too short time for proper new bone formation, which in the case of cancellous bone is at least 6 weeks.

Accordingly, there is need for a method of enhancing drug release from a synthetic, bioabsorbable product, which has tissue supporting function, high mechanical strength and releases drug in therapeutic doses over several weeks or months.

SUMMARY OF THE INVENTION

In an embodiment, the present invention provides a method of increasing a drug release rate from a composite material comprising providing a bioabsorbable polymer matrix and adding a drug to the bioabsorbable polymer matrix to form a composite material. The method further comprises deforming the composite material at a temperature above the glass transition temperature of the bioabsorbable polymer matrix to form an oriented composite material. The oriented composite material has a higher drug release rate than a non-oriented composite material comprising the same bioabsorbable polymer matrix and the same drug as the oriented composite material. The non-oriented composite material comprising the same bioabsorbable polymer matrix and the same drug as the oriented composite material means that the non-oriented composite material has the same type and amount of bioabsorbable polymer matrix and the same type and amount of drug as the oriented composite material. In other words, the non-oriented and oriented composite materials only differ in that the oriented composite material is subject to a solid state deformation process and the non-oriented composite material is not.

In another embodiment, the present invention provides a method of enhancing a drug release rate from a composite material comprising forming a mixture of a polymer melt and drug particles dispersed into the polymer melt by melt mixing. The method further comprises pressing the mixture through a die to form a pressed composite material, cooling the pressed composite material to solidify the pressed composite material into a solid composite material and drawing mechanically the solid composite material at a temperature above the glass transition temperature of the polymer melt to orient the solid composite material longitudinally and form an oriented composite material. The oriented composite material has a higher drug release rate than a non-oriented composite material comprising the same polymer melt and the same drug particles as the oriented composite material.

DETAILED DESCRIPTION OF THE INVENTION

Figure 1A:
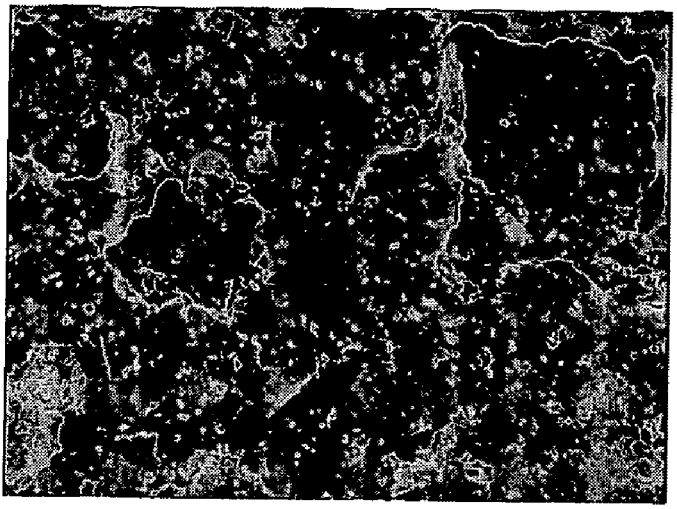
FIG. 1A is a SEM image of the fractured surface of a P(L/DL) LA melt-compounded billets containing ciprofloxacin. The fractured surface is along the longitudinal axis of the billet and the magnification is 1500×.

This invention describes a method to enhance drug release from drug-releasing materials, such as drug-releasing implants. According to this method, a composite material comprising a bioabsorbable polymer matrix and a drug particle phase dispersed therein is deformed in the solid state, i.e. at a temperature which is above the glass transition temperature (Tg) of the polymer matrix, resulting in orientation of the structure of the polymer matrix. Surprisingly, solid state deformation of a composite biomaterial significantly enhances drug release from the polymer matrix in hydrolytic conditions. The drug release, which may in an otherwise comparable non-deformed composite material be below the therapeutic level, can be enhanced even to the therapeutic level with the deformation procedure, which increases significantly the efficacy and application possibilities of bioabsorbable drug-releasing implants.

The method of the present invention can be used to manufacture synthetic bioabsorbable, surgical materials such as, for example, tissue fixation implants or guided tissue regeneration devices. Such tissue fixation implants include bone-to-bone, bone-to-soft tissue, and soft tissue-to-soft tissue fixation implants. Non-limiting examples of bone-to bone fixation implants include pins, screws, plates, tacks, or intramedullary nails. Non-limiting examples of bone-to-soft tissue and soft tissue-to-soft tissue fixation implants include screws, tacks, bolts, suture anchors, arrows and clamps, meshes, membranes and tissue anchors, like interference screws or wedges. Specific non-limiting geometries of implants are described extensively in the literature, e.g. in U.S. Pat. No. 4,968,317; EPO Pat. No. 0423155; EPO Pat. Appl. No. 449867; U.S. Pat. No. 5,562,704; FI Pat. Appl. No. 98136; FI Pat. Appl. 965111; U.S. patent application Ser. No. 08/873,174; U.S. patent application Ser. No. 08/887,130; U.S. patent application Ser. No. 08/914,137; U.S. patent application Ser. No. 08/997,458; U.S. patent application Ser.

No. 09/055,005; U.S. patent application Ser. No. 09/033,475; U.S. patent application Ser. No. 09/036,259; U.S. patent application Ser. No. 09/152,437, and in references mentioned in the above patents and patent applications, all of which are incorporated by reference herein.

Such implants can be used, for example, with compromised bone or with other musculoskeletal tissue. Non-limiting examples of compromised bone includes infected and/or fractured bone or other bone damage. Non-limiting examples of other musculoskeletal tissue include infected and/or ruptured ligaments, tendons or other connective tissue.

The surgical materials according to the methods of the present invention have a high shear strength and accelerated drug-release behavior in hydrolytic conditions, when compared to non-deformed materials and implants. One particular advantage of the drug releasing implants according to the methods of the present invention is that they can be used for the reduction of tissue damages, like connective tissue damages and bone fractures and for the simultaneous prevention and/or treatment of infection, such as the prevention of a bone infection like osteomyelitis.

Although the methods of the present invention are suitable for any type of patients, particularly suitable patients are patients with bone fractures and/or patients who need osteotomies and have a high risk of developing an infection after operation. Other particularly suitable patients are those that are immunocompromised; diabetic patients; patients with poor blood circulation in the extremities; patients with vascular disease; patients on immunosuppressive medications such as transplant patients; patients on steriod medications; cancer patients; and older patients.

The polymeric matrix of the composite material according to the methods of the present invention can be any suitable polymer such as a homopolymer, a copolymer, a terpolymer, or a polymers alloy, all of which are described extensively in the art. Such polymers can be selected, for example, from poly-α-hydroxy acids (e.g. polylactides, polyglycolides and their copolymers), polyanhydrides, polyorthoesters, segmented block copolymers of polyethylene glycol and polybutylene terephtalate (POLYACTIVE™), tyrosine derivative polymers or poly(ester-amides). Other suitable polymers are mentioned in U.S. Pat. Nos. 4,968,317; 5,618,563; FI Pat. No. 98136; FI Pat. No. 100217B; and in "Biomedical Polymers" edited by S. W. Shalaby, Carl Hanser Verlag, Munich, Vienna, New York, 1994 and in many references cited in the above publications, as also in many other publications mentioned earlier, all of which are incorporated by reference herein.

A variety of drug(s), like antibiotics, can be used in the composite material according to the methods of the present invention for treating and/or preventing infection. Suitable antibiotics may be selected from aminoglycoside antibiotics or quinolones or beta-lactams, such as cefalosporines, ciprofloxacin, gentamycin, tobramycin, erythromycin, vanmycin, oxacillin, cloxacillin, methicillin lincomycin, ampicillin, and colistin, although others may be used as well. Other suitable antibiotics have been described in the literature (P. Rokkanen et al. "Traumatologia" (Traumatology), Kandidaattikustannus Oy, Helsinki, Finland, 1995, p. 103-104 or J. H. Calhoun and J. T. Mader (eds.) "Musculoskeletal Infections", Marcel Dekker, Inc., New York, USA, p. 495-528) as also in several, above mentioned, all of which are incorporated by reference herein. Preferably, the drug is 1 to 20 weight percent of the composite material. Preferably, the drug is released from the composite material in therapeutic concentrations for a period of at least four weeks or more in hydrolytic conditions. Therapeutic concentrations are concentrations sufficient to produce the desired therapeutic effect, such as, for example, inhibiting or preventing infection. Preferably, the drug is an antibiotic that is released at a level of at least 2 milligrams/liter (mg/l) after four weeks in hydrolytic conditions.

There are several technologies available to manufacture the composite material according to the methods of the present invention. The drug(s) can be in the form of powders, granules, flakes or fibers or in other particle forms and can be mixed mechanically with the polymer matrix and the resultant composite material can be heated and processed by methods of polymer technology. Such polymer technology methods include compounding by a batch mixer (e.g. by a Brabender-, Banbury-, Farrel- or Sigma-type mixer); continuous extrusion using, for example, a single- or twin-screw extruder or a special conical screw extruder; injection molding (continuous or non-continuous); compression molding; or ultrasonic compression so that the polymeric matrix melts or softens and the drug is dispersed into the melted polymer matrix. The composite material can then be formed to a continuous billet, such as, for example, a cylindrical, rectangular or plate-like elongated billet and cooled (below the melting temperature in the case of crystallizable polymers) to solidify the billet. The composite material can be cooled and solidified also by injecting the material into a mold (with an injection molding or transfer molding machine) and cooling it inside of the mold. Thereafter, the billet is oriented with a solid state deformation process, such as, for example, drawing, twisting, shearing, compressing, rolling, hydrostatically extruding, or ram extruding to create an orientation of the polymer matrix around drug particles. Surprisingly, this orientation of the polymer matrix accelerates significantly the release rate of the drug from the polymer matrix.

Another manufacturing method is to pelletize or to granulate the composite material or to crush it to particles after cooling it to room temperature (RT), for example. The composite material can be crushed at RT or after additional cooling with liquid nitrogen, for example. The crushed powder can be sieved to desired size fractions. The pelletized, granulated or crushed composite material can then be melt processed to an elongated billet and cooled below the melting temperature of the polymer matrix to solidify the billet. Thereafter, the billet can be oriented with a solid state deformation method to form an oriented composite material and to accelerate drug release from the polymer matrix.

Other manufacturing methods include composite fabrication techniques, like lamination, film stacking, injection, powder impregnation, co-weaving and knitting, pultrusion and filament winding of oriented or non-oriented fibers and/or films or membranes made of a polymer matrix and a drug(s) to obtain a high-strength, oriented, drug-releasing bioabsorbable composite material.

The composite material according to the methods of the present invention can also be in the form of spheres (beads), cylinders or ellipsoids (diameter or dimensions typically between 1-7 mm), which can be manufactured from solid state deformed billets such as by crushing or cutting the billet to pieces, for example. Such particles can be used to fill infected and purified bone defects, holes and gaps. Because of the strong and tough structure of such particles, they can be filled tightly into bone defects even in load bearing bones. They can also be combined with gels, lotions, or pastes, which optionally may contain bone growth factors (BMP), to facilitate the new bone formation effect and/or to make the handling of composite material more easy.

The beads and/or cylinders can also be bound to each other with a bioabsorbable mono- or multifilament bioabsorbable wire to make a pearl-like systems that can be placed inside of bone defects.

Preferably, the composite material comprises pores. Such pores can be created by adding solid drug particles to the polymer matrix. If the drug is disposed into the polymer matrix as solid particles, then the drug particles do not elongate during drawing and therefore elongated pores are formed around the drug particles as a consequence of the drawing.

EXAMPLES

Example 1

Materials

A composite material of a bioabsorbable polymer matrix and antibiotic were studied. The bioabsorbable polymer matrix was RESOMER® LR708 (Boehringer Ingelheim, Germany), which is an amorphous synthetic poly-L-lactide-co-DL-lactide (P(L/DL)LA 70:30) with inherent viscosity of 6.3 dl/g (in 0.1% chloroform, at 25° C.). The drug was the antibiotic ciprofloxacin (Jinxing Kangle Pharmaceutical Factory, China).

Manufacturing

The bioabsorbable polymer matrix was extruded into cylindrical billets (rods) by melt compounding using a small laboratory scale melt mixer (Neste Corporate, R&D, Finland). The diameter of the compounded billets was 6.4 mm. After melt compounding, the billets were cooled to RT. Ciprofloxacin was dispersed (as small white particles) into the melt compounded billets, as is seen from FIG. 1A.

Figure 1B:
FIG. 1B is a SEM image of the fractured surface of a P(L/DL) LA oriented billets containing ciprofloxacin. The fractured surface is along the longitudinal axis of the billet and the magnification is 1500×.

Some of the billets were oriented by die-drawing them at 72° C. into oriented rods, with a diameter of 3.0 mm. (the draw ratio was 4.4±0.1). Ciprofloxacin was also dispersed into the microstructure of the oriented rods. The oriented rod showed fibrillated structure as seen in FIG. 1B. The remaining billets were not oriented.

Characterization

Microstructure and component dispersion of the oriented rods and non-oriented billets were determined using scanning electron microscopy (SEM). The initial ciprofloxacin content of the samples was determined spectrophotometrically using tricholoromethane as a solvent. It was determined that the initial ciprofloxacin content was 8 weight %. To determine the concentrations of ciprofloxacin released in vitro, samples (500 mg) were placed into phosphate buffer ($KH_2PO_4$ and NaOH) at pH of 7.4. Five parallel samples were kept in a heating chamber at a temperature of 37° C. At specific sampling times, the buffer solution was replaced with fresh buffer and released antibiotic concentrations were measured using a UNICAM UV 500 spectrometer (Unicam Instruments, Cambridge, UK) at $\lambda=270.5$ nm according to the Beer-Lambert Law. Ciprofloxacin was microbiologically proved to be bioactive after manufacturing and during the in vitro drug release tests.

Initial shear strengths of the oriented rods and non-oriented billets were measured at room temperature (RT) with the method described in P. Törmälä, et al., *J. Biomed. Mater. Res.*, Vol. 25, 1-22 (1991).

Results

The initial shear strength of the non-oriented billets was 39±2 MPa at RT, while the initial shear strength of the oriented rods had increased to 101±4 MPa.

Figure 2:
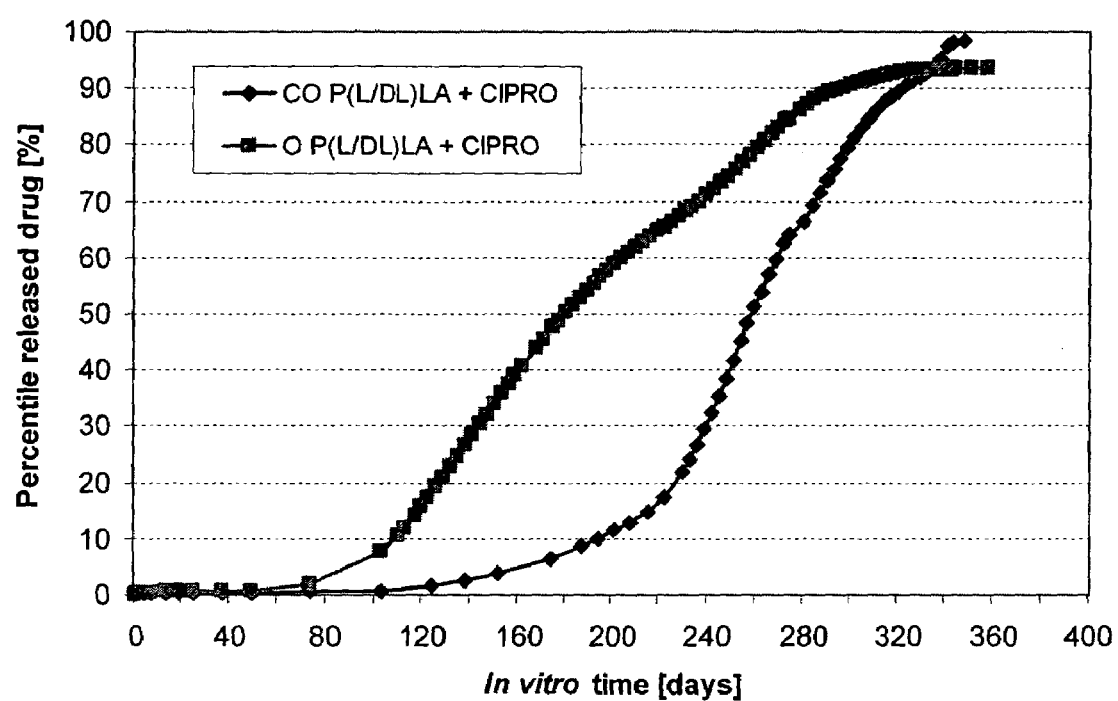
FIG. 2 is a chart of the percentage of released ciprofloxacin from melt-compounded (non-oriented) P(L/DL) LA billets (CO P(L/DL) LA+CIPRO) and from oriented P(L/DL) LA billets (O P(L/DL)LA+CIPRO).

The oriented rods released ciprofloxacin much more rapidly when compared to the drug release from the non-oriented billets. For example, during the first 150 days in vitro only 3.8% of loaded drug was released from the non-oriented billets while 34% of loaded drug was released from the oriented rods. Thus, the orientation of the rod structure accelerated the ciprofloxacin release rate almost 10-fold when compared to the non-oriented billets containing the same type and amount of polymer matrix and the same type and amount of drug as the oriented rods. Drug release rates from ciprofloxacin containing non-oriented billets (CO) and oriented (O)P(L/DL)LA rods are shown in FIG. 2.

Example 2

Materials

Non-oriented billets and oriented billets (rods) of bioabsorbable semicrystalline poly(lactide-co-glycolide) 80:20 (PURASORB® PLG of CCA Purac, Holland with inherent viscosity of 6.3 dl/g in 0.1%, chloroform at 25° C.) (PLGA) and ciprofloxacin (Jinxing Kangle Pharmaceutical Factory) were studied.

Manufacturing

The bioabsorbable polymer matrices were extruded (compounded) into cylindrical billets using a small laboratory scale mixer (Neste Corporate, R&D, Finland). The diameter of the melt compounded billets was 6.4 mm. After compounding, the billets were cooled to RT. Some of the billets were heated again and die-drawn at 72° C. to oriented (O) billets (rods), with the final diameter being 3.0 mm. The draw ratio was 4.4±0.1. The remaining billets were not oriented. Studied drug release test samples were sterilized using gamma radiation with a radiation dose of 25 kGy.

Characterization

Microstructure and component dispersion of the oriented rods and non-oriented billets were determined using scanning electron microscopy (SEM). The initial ciprofloxacin content of the samples was determined spectrophotometrically using tricholoromethane as a solvent. It was determined that the initial ciprofloxacin content was 8 weight %. To determine the concentrations of ciprofloxacin released in vitro, samples (500 mg) were placed into phosphate buffer ($KH_2PO_4$ and NaOH) at pH of 7.4. Five parallel samples were kept in a heating chamber at a temperature of 37° C. At specific sampling times, the buffer solution was replaced with fresh buffer and released antibiotic concentrations were measured using a UNICAM UV 500 spectrometer (Unicam Instruments, Cambridge, UK) at $\lambda=270.5$ nm according to the Beer-Lambert Law. Ciprofloxacin was microbiologically proved to be bioactive after manufacturing and during the in vitro drug release tests.

Initial shear strengths of the oriented rods and non-oriented billets were measured at room temperature (RT) with the method referred to in Example 1.

Results

The initial shear strength of the non-oriented billets was 38±3 MPa at RT, while the initial shear strength of the oriented rods had increased to 90±4 MPa.

Figure 3A:
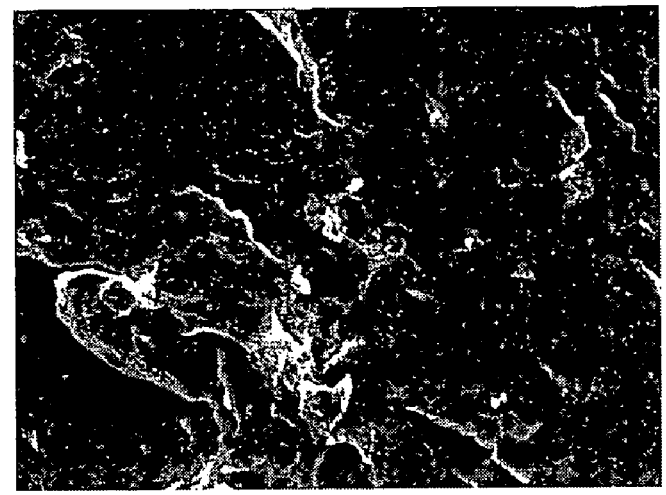
FIG. 3A is an SEM image of a fractured surface of a PLGA melt-molded billet at a magnification of 500×.
Figure 3B:
FIG. 3B is an SEM image of a fractured surface of a PLGA oriented billet at a magnification of 1500×.

FIGS. 3A and 3B show the internal microstructure of ciprofloxacin containing non-oriented rods (FIG. 3A) and oriented (O) (FIG. 3B) billets. Ciprofloxacin can be seen as small dispersed particles in both cases.

Figure 4:
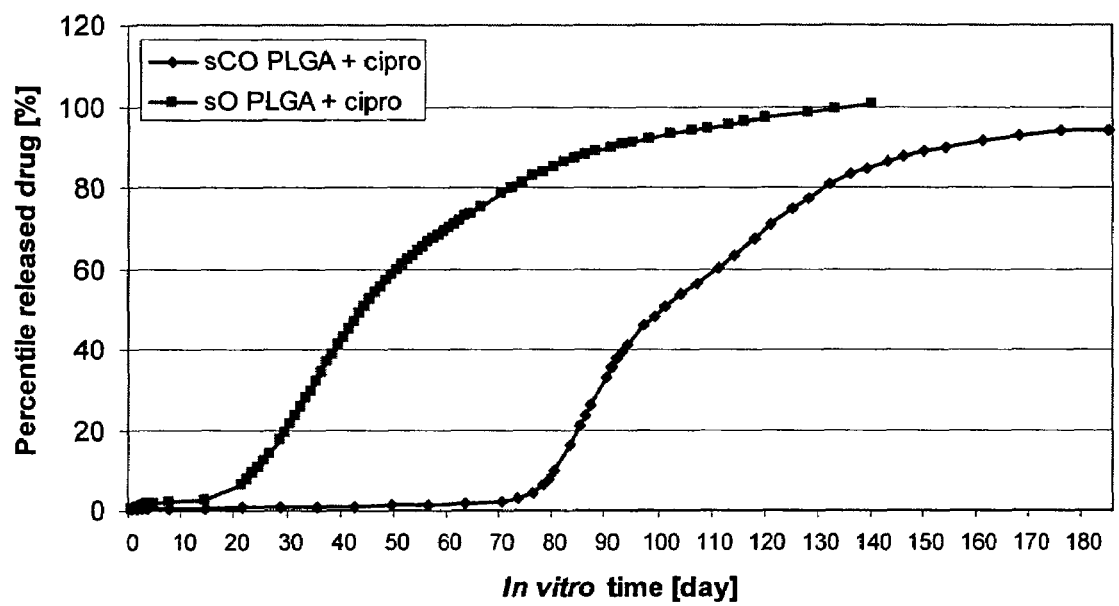
FIG. 4 is a chart of the percentage of released ciproflaxacin from melt-compounded (non-oriented) PLGA billets (sCO PLGA+Cipro) and from oriented PLGA billets (sO PLGA+Cipro).

Orientation of PLGA+ciprofloxacin billets increased dramatically the release of ciprofloxacin from the polymer matrix when compared to the drug release from the non-oriented billets. For example, during the first 50 days in vitro only 1.8% of loaded drug was released from the non-oriented billets while 59% of loaded drug was released from the oriented billets. Drug release rates from ciprofloxacin containing non-oriented PLGA billets (CO) and oriented (O) billets are shown in FIG. 4.

The foregoing description and examples have been set forth merely to illustrate the invention and are not intended as being limiting. Each of the disclosed aspects and embodiments of the present invention may be considered individually or in combination with other aspects, embodiments, and variations of the invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

We claim:

1. A method of manufacturing an oriented composite material comprising:
   providing a bioabsorbable polymer matrix;
   adding a drug to the bioabsorbable polymer matrix to form a composite material;
   orienting the composite material by a solid state deformation process at a temperature above the glass transition temperature of the bioabsorbable polymer matrix to form an oriented composite material; and
   comparing the drug release rate of the oriented composite material with the drug release rate of a non-oriented composite material comprising the same bioabsorbable polymer matrix and the same drug as the oriented composite material, wherein the oriented composite material has a higher drug release rate.

2. The method of claim 1, wherein the oriented composite material comprises pores.

3. The method of claim 1, wherein the oriented composite material is an implant.

4. The method of claim 3, wherein the implant is a bone-to-bone implant, a soft tissue-to-bone implant, or a soft tissue-to-soft tissue implant.

5. The method of claim 3, wherein the implant is a pin, screw, plate, tack, intramedullary nail, bolt, suture anchor, arrow, or tissue anchor.

6. The method of claim 5, wherein the tissue anchor is an interference screw or wedge.

7. The method of claim 1, wherein the drug comprises 1 to 20 weight percent of said composite material.

8. The method of claim 1, wherein the drug is an antibiotic.

9. The method of claim 8, wherein the antibiotic is ciprofloxacin.

10. The method of claim 1, wherein the oriented composite material has an at least partially fibrillar structure.

11. A method of treating or preventing a bone infection comprising using the oriented composite material manufactured according to the method of claim 1.

12. The method of claim 11, wherein the bone infection is osteomyelitis.

13. A method of repairing an infected bone fracture comprising using the oriented composite material manufactured according to the method of claim 1.

14. A method of performing an osteotomy in a patient with a high risk of infection comprising using the oriented composite material manufactured according to the method of claim 1.

15. A method of manufacturing an oriented composite material comprising:
   forming a mixture of a polymer melt and drug particles dispersed into the polymer melt by melt mixing;
   pressing the mixture through a die to form a pressed composite material;
   cooling the pressed composite material to solidify the pressed material into a solid composite material; and
   drawing mechanically the composite material in solid state at a temperature above the glass transition temperature of the polymer melt to orient the solid composite material longitudinally and form an oriented composite material; and
   comparing the drug release rate of the oriented composite material with the drug release rate of a non-oriented composite material comprising the same polymer melt and the same drag particles as the oriented composite material, wherein the oriented composite material has a higher drug release rate.

* * * * *